(12) United States Patent
Boucher

(10) Patent No.: US 11,193,861 B2
(45) Date of Patent: Dec. 7, 2021

(54) WASTEWATER TREATMENT SAMPLING DEVICE

(71) Applicant: 11814192 CANADA INC., Sherbrooke (CA)

(72) Inventor: Benoit Boucher, Sherbrooke (CA)

(73) Assignee: 11814192 Canada Inc., Sherbrooke (CA)

( * ) Notice: Subject to any disclaimer, the term of this patent is extended or adjusted under 35 U.S.C. 154(b) by 0 days.

(21) Appl. No.: 17/063,163

(22) Filed: Oct. 5, 2020

(65) Prior Publication Data

US 2021/0063290 A1   Mar. 4, 2021

Related U.S. Application Data

(63) Continuation of application No. PCT/CA2020/050577, filed on Apr. 30, 2020.

(60) Provisional application No. 62/895,842, filed on Sep. 4, 2019.

(51) Int. Cl.
| | | |
|---|---|---|
| *G01N 1/34* | (2006.01) | |
| *C02F 3/28* | (2006.01) | |
| *G01N 33/18* | (2006.01) | |
| *C02F 101/32* | (2006.01) | |

(52) U.S. Cl.
CPC .............. *G01N 1/34* (2013.01); *C02F 3/288* (2013.01); *G01N 33/18* (2013.01); *C02F 2101/32* (2013.01)

(58) Field of Classification Search
CPC ...................................................... C02F 3/288
USPC ...................................................... 73/64.56
See application file for complete search history.

(56) References Cited

U.S. PATENT DOCUMENTS

| | | | | |
|---|---|---|---|---|
| 5,140,855 A | * | 8/1992 | Gruber .................... | C02F 3/327 73/432.1 |
| 5,360,556 A | * | 11/1994 | Ball ........................ | C02F 3/046 210/804 |
| 6,581,336 B2 | | 6/2003 | Anttalainen et al. | |
| 7,867,396 B2 | * | 1/2011 | Hill ........................... | C02F 3/04 210/602 |

(Continued)

FOREIGN PATENT DOCUMENTS

| | | |
|---|---|---|
| CN | 204781259 | 11/2015 |
| CN | 105527127 | 4/2016 |

(Continued)

OTHER PUBLICATIONS

International Search Report dated Aug. 18, 2020, International application No. PCT/CA2020/050577.

*Primary Examiner* — Daniel S Larkin
(74) *Attorney, Agent, or Firm* — Brouillette Legal Inc.; Robert Brouillettte

(57) ABSTRACT

A wastewater sampling device configured to collect, for sampling purposes, a portion of an effluent and/or of treated wastewater released by a wastewater treatment system. The wastewater sampling device comprises a base and sidewalls configured to receive and channel the effluent and/or treated wastewater into a collection well whereby said effluent and/or treated wastewater may be subsequently collected by means of a collection chimney. The wastewater sampling device may be installed at any depth underneath the wastewater treatment system, thus allowing for a collection of effluent and/or treated wastewater at different stages within the filtering process.

25 Claims, 13 Drawing Sheets

(56) References Cited

U.S. PATENT DOCUMENTS

| | | | | |
|---|---|---|---|---|
| 9,670,071 B2 * | 6/2017 | Przekop | ................ | B01D 29/90 |
| 2004/0206162 A1 * | 10/2004 | Shedd | ................ | G01N 33/186 |
| | | | | 73/53.01 |
| 2017/0219132 A1 | 8/2017 | Douglass, III | | |

FOREIGN PATENT DOCUMENTS

| | | |
|---|---|---|
| CN | 107381667 | 11/2017 |
| CN | 110028159 | 7/2019 |
| DE | 2559476 | 12/1976 |
| JP | 200296395 | 10/2000 |
| KR | 100964741 | 6/2010 |
| WO | WO2006123868 | 11/2006 |

* cited by examiner

WASTEWATER TREATMENT SAMPLING DEVICE

CROSS-REFERENCE TO RELATED APPLICATIONS

The present patent application is a continuation of PCT Application No. PCT/CA2020/050577, entitled "WASTEWATER TREATMENT SAMPLING DEVICE" and filed with the World Intellectual Property Organization on Apr. 30, 2020, the PCT Application and the present patent application claim the benefit of priority of U.S. Provisional Patent Application No. 62/895,842, entitled "WASTEWATER TREATMENT SAMPLING DEVICE" filed at the United States Patent and Trademark Office on Sep. 4, 2019, the contents of which are incorporated herein by reference.

FIELD OF THE INVENTION

The present invention generally relates to the field of wastewater and sewage treatment. More particularly, the present invention concerns a device and method for collecting treated wastewater and sewage water for testing purposes. The device is easily installable in a wastewater treatment field, allowing the sampling device to be used to capture, sample and infiltrate system effluent.

BACKGROUND OF THE INVENTION

In the field of wastewater treatment, sampling devices are typically used to collect and store treated wastewater for future retrieval and testing by a maintenance professional or technician. Such collection may be necessary to ensure a proper functioning of the wastewater treatment device and compliance with potential regulations regarding the contamination of drainage fields and surrounding soil.

Various wastewater sampling devices have been proposed for the collection of treated wastewater from a wastewater treatment field. For example, U.S. Pat. No. 6,372,128 discloses a sampling system installed at the base of a biofiltering device enclosed within a housing. The biofiltering device is confined within sidewalls and top wall formed of concrete creating a structural housing for the treatment of wastewater. The sampling system disclosed therein comprises a horizontal tray-like member configured to channel a portion of the treated wastewater through an aperture in the housing and into a sampling hole.

U.S. Pat. No. 6,506,298 also discloses a sampling system installed at the base of a biofiltering device enclosed within a housing. Such a sampling device comprises a horizontal tray-like member configured to channel a portion of the treated wastewater through a drip conduit in fluid flow communication with a sampling hole located outside of the housing.

The use of the aforementioned sampling devices presents certain drawbacks, namely the requirement of an enclosing housing capable of providing structural support for the sampling device. In order to reduce costs and offer accessible solutions for wastewater treatment, many wastewater treatment systems comprise septic drain fields which may be installed in shallow trenches in an open field without being enclosed in rigid structures. There is therefore a need for a wastewater sampling device capable of being freely installed in a drainage field without any surrounding support structures.

SUMMARY OF THE INVENTION

The present invention is directed to a wastewater treatment sampling device. The sampling device is configured for installation under the ground surface for the collection of sampling wastewater and comprises a base comprising side walls configured to receive the sampling wastewater, the side walls vertically extending above the base by a height suitable to prevent the received sampling wastewater from being conveyed outside of the base, a collection well downwardly extending from the base, the collection well being adapted to collect the sampling wastewater and a sampling chimney in fluid communication with the collection well and adapted to allow access to the sampling wastewater collected within the collection well.

The base and the collection well may be unitary, the side walls may comprise flanges, the sampling chimney may comprise a lower base portion in fluid communication with the collection well and/or the lower base portion may comprise a filter. The lower base portion may further comprise an opening with the filter stretching over the opening.

The base may further comprises ribs, the side walls may comprise ribs, the wastewater treatment sampling device may comprises a ramp adapted to channel sampling wastewater from the base to the collection well and/or the collection well may comprise a perforated collection well base adapted to allow a release of the sampling wastewater. The collection well base may be lower than the base of the sampling device. Moreover, the sampling device may be made of semi-rigid material such as plastic, the side walls may form a continuous wall and/or the collection well may extend from a side wall at its center. The side walls may vertically extend above the base by a height of at least 25 cm.

In another aspect of the invention, a method of collecting treated wastewater for sampling within a wastewater treatment system is provided. The method comprises capturing in a sampling device some of the treated wastewater percolating under the treatment system, channelling the captured wastewater from a base of the sampling device to a collection well using a ramp at an angle and collecting the channelled wastewater through a collection chimney in fluid communication with the collection well.

The method further may further comprise filtering the channelled wastewater, channelling the collected wastewater from the base of the sampling device around the chimney inserted into the collection well, channelling the collected wastewater from the base of the sampling device below the chimney inserted into the collection well and/or burying the sampling device in an open drainage field.

The features of the present invention which are believed to be novel are set forth with particularity in the appended claims.

BRIEF DESCRIPTION OF THE DRAWINGS

The above and other objects, features and advantages of the invention will become more readily apparent from the following description, reference being made to the accompanying drawings in which.

DETAILED DESCRIPTION OF THE PREFERRED EMBODIMENT

A novel wastewater treatment sampling device will be described hereinafter. Although the invention is described in terms of specific illustrative embodiments, it is to be understood that the embodiments described herein are by way of example only and that the scope of the invention is not intended to be limited thereby.

Figure 1:
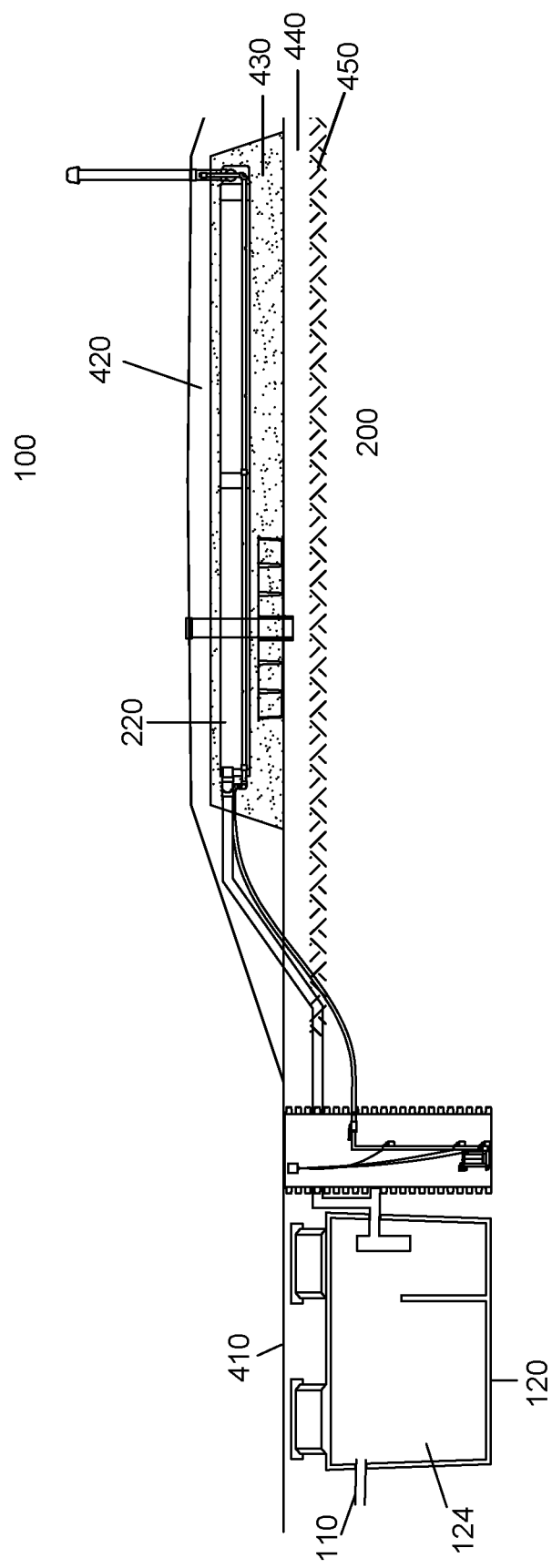
FIG. 1 is a side view of an embodiment of a wastewater treatment system for the decontamination and processing of liquid waste in accordance with the principles of the present invention.

Referring now to FIG. 1, an embodiment of a wastewater treatment system 100 for the decontamination and processing of liquid waste is illustrated. The wastewater treatment system 100 typically comprises an input source, such as an input source or drainage pipe 110, a tank 120, such as a septic tank, and a drainage field 200.

The drainage pipe 110 may be configured to deliver wastewater to the wastewater treatment system 100 from a water consuming environment (such as a residential dwelling, a commercial space, an industrial space, etc.) in areas that are not connected to a municipal or urban sewage system such as, but not limited to, rural areas. The wastewater may comprise any water used from domestic, industrial, commercial or agricultural activities or any combination thereof.

Still referring to FIG. 1, in some embodiments, the drainage pipe 110 may be fluidly connected to the septic tank 120. The septic tank 120 may comprise an underground chamber 124 configured as a water-tight container generally made of concrete, fiberglass, plastic or any other suitable material known in the art. The underground chamber 124 may be either partially or entirely buried underneath a surface 410, such as a finished ground surface.

Figure 2:
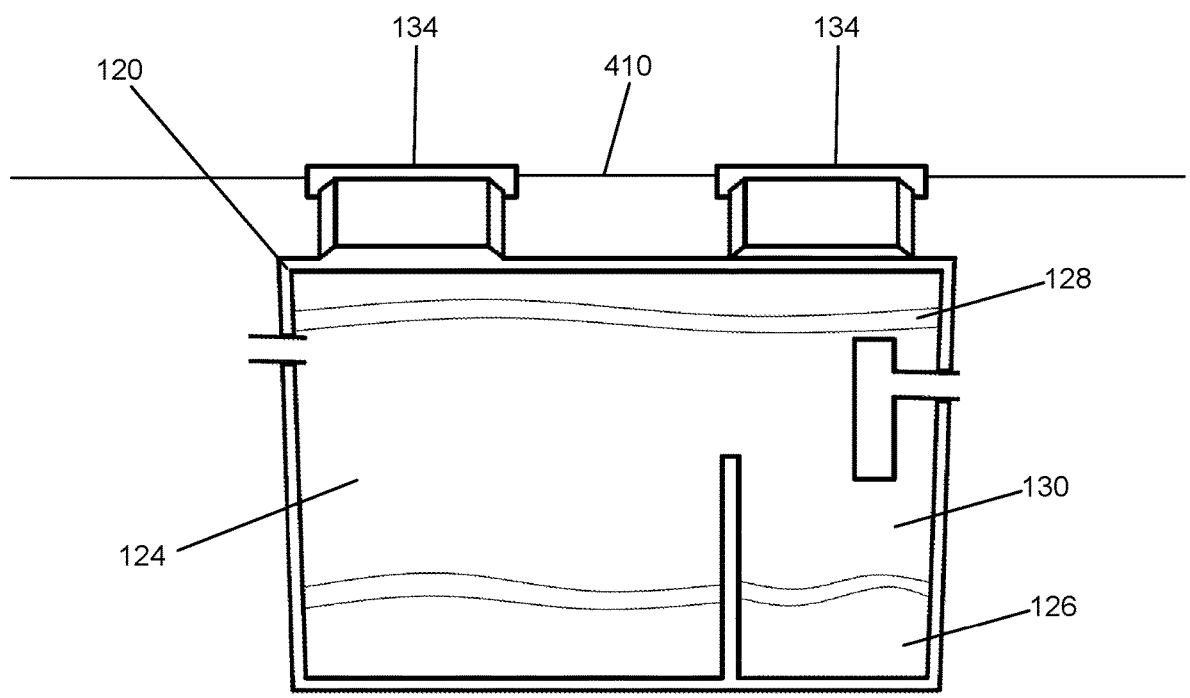
FIG. 2 is a cross-sectional view of an exemplary septic tank used in the system of FIG. 1.

Referring now to FIG. 2, in some embodiments, the flow of wastewater within the septic tank 120 may be slow enough to allow for settling. Such flow of wastewater may further allow anaerobic processes to take place as a primary treatment of the wastewater. The settling process occurring within the underground chamber 124 will usually allow for solids and heavier particles disposed within the wastewater to settle to the bottom of the underground chamber 124 to form a layer of sludge 126. The septic tank 120 may further comprise microbes adapted to break down the sludge 126 by means of an anaerobic digestion into high molecular weight hydrocarbons, methane, hydrogen sulfide and sulfur dioxide gases. The microbes disposed within the septic tank 120 may include, but are not limited to, bacteria, fungi, algae, protozoa, rotifers and nematodes.

The settling process occurring within the underground chamber 124 may further allow separation of oils and grease from the wastewater, such as allowing said oils and grease to rise or float above the other components of the wastewater and to form a layer of scum 128. The scum 128 may further comprise other particles which are less dense than water including, but not limited to, soap scum, hair and paper products such as facial tissues.

In some embodiments, the remaining components of the wastewater which have not settled to the bottom underground chamber 124 to form a part of the layer of sludge 126 or risen to form a part of the layer of scum 128 may form a third intermediate layer of effluent 130.

In further embodiments, the septic tank 120 may further comprise one or more access hatches for accessing the underground chamber 124. For example, in the embodiment shown in FIG. 2, the septic tank 120 comprises an access hatch 134. The access hatch 134 may be positioned above the surface 410 or below the surface 410 and accessible with little or no digging. The access hatch 134 may allow access to the underground chamber 124 to allow for drainage of the accumulation of the scum 128 and the sludge 126 which has not been decomposed by anaerobic digestion or for any other general maintenance of the septic tank 120.

Figure 3:
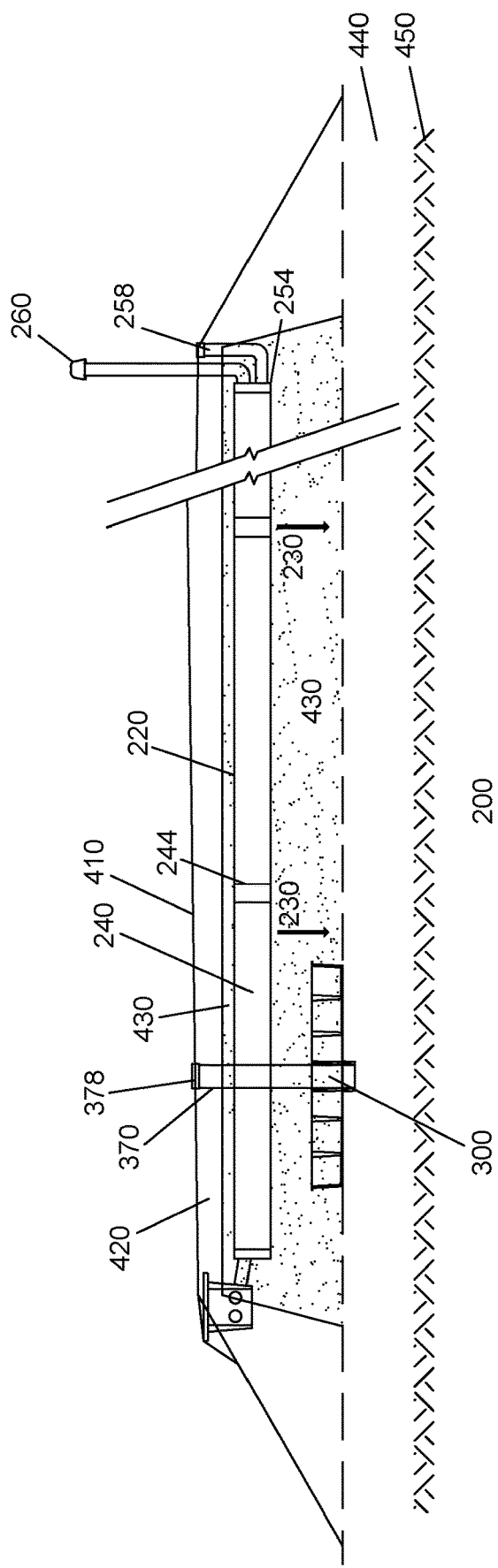
FIG. 3 shows a side perspective view of an exemplary of a drainage field used in the system of FIG. 1.

Referring now to FIGS. 1 and 3, in some embodiments, the septic tank 120 may be fluidly connected to one or more drainage fields 200 configured to receive and treat the effluent 130 from the septic tank 120 into treated wastewater 230. For example, in the embodiment shown in FIG. 1, the wastewater treatment system 100 comprises a drainage field 200 configured to treat the effluent 130. In other embodiments, the one or more drainage fields 200 may comprise a septic field, a polishing field, a seepage field or any other type of infiltration field adapted to receive treated or untreated wastewater.

Now referring to FIG. 3, the drainage field 200 may comprise a leach system 220 disposed between a plurality of ground layers. The drainage field 200 comprises a surface 410, a covering layer 420 immediately below the ground surface 410, a filtering medium 430, a permeable soil layer 440 and a bedrock layer 450. In some embodiments, one or more of the layers may overlap and combine thereby removing any clear delineation between them.

In some embodiments, the leach system 220 may be at least partially surrounded by the filtering medium 430. In yet other embodiments, a portion of the filtering medium 430 may be disposed above the leach system 220 and/or another portion of the filtering medium 430 may be disposed underneath the leach system 220.

Figure 4:
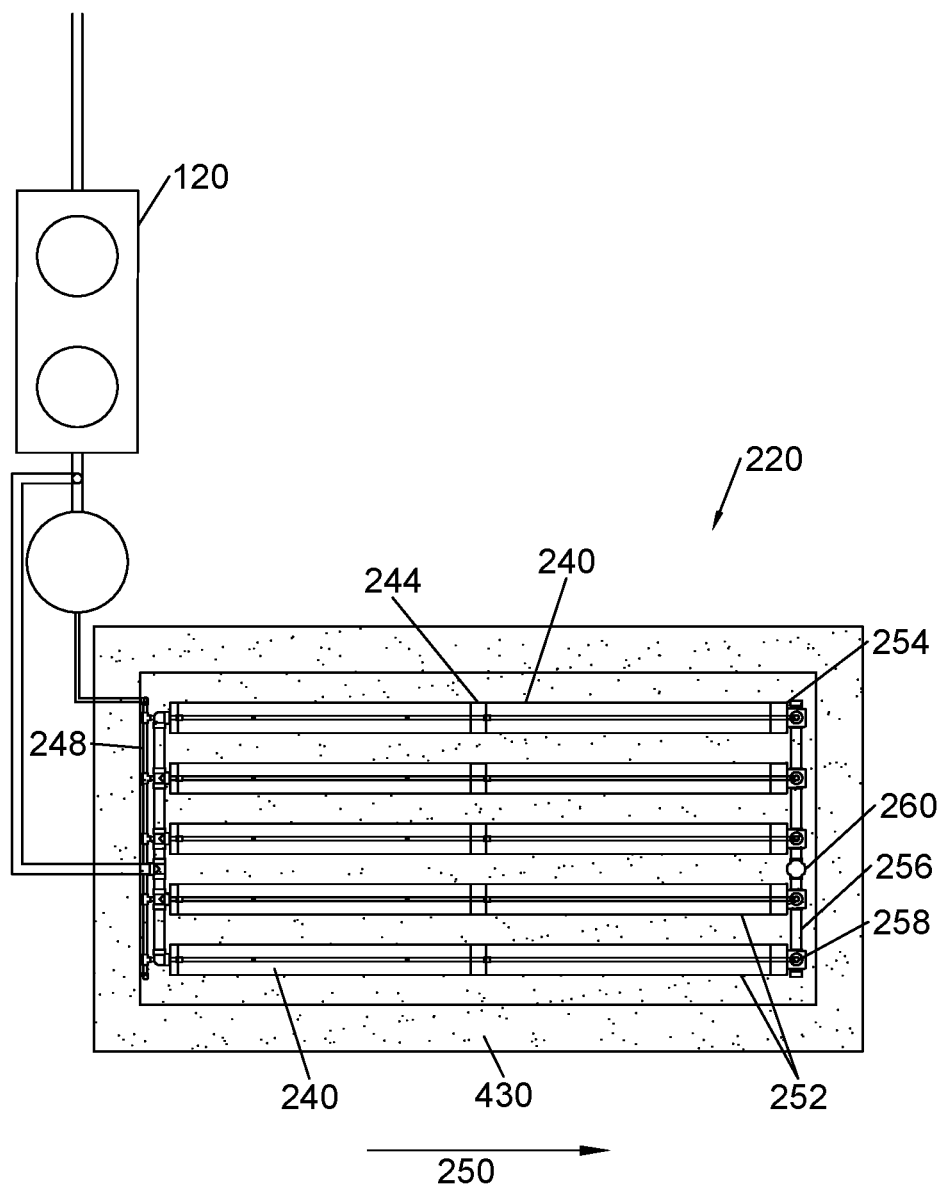
FIG. 4 is a top perspective view of the drainage field of FIG. 3.

Now referring to FIG. 4, in some embodiments, the leach system 220 may comprise one or more drainage passages or conduits 240 configured to treat the effluent 130. The drainage conduits 240 may comprise pipes configured to carry and distribute the effluent 130 across the drainage field 200. In some embodiments, the pipes may be perforated pipes. The effluent 130 flowing in the drainage conduits 240 are generally conveyed by gravitational forces in tandem with the geometry of the drainage conduits 240.

The drainage conduits 240 may have any cross-sectional shape adapted to accommodate the volume of water to be disposed supplied by the drainage pipe 110 and/or to accommodate the topographic requirements of the installation site.

For example, in the present embodiment, the drainage conduits 240 are circular. It may be appreciated that the drainage conduits 240 may have any other cross-sectional shape known in the art.

The drainage conduits 240 may be made of any semi rigid material. Examples of possible construction materials include, but are not limited to, plastics such as polypropylene and polyethylene or flexible metal. Other polymers, fibrous material, metal, rubber or rubber-like materials may also be used.

In yet other embodiments, the drainage conduits 240 may have any length or cross-sectional area suitable to accommodate the volume of water to be disposed supplied by the drainage pipe 110 and/or to accommodate the topographic requirements of the installation site. In some embodiments, the drainage conduits 240 may have a cross-sectional area of 175 cm$^2$ to 2,000 cm$^2$.

In some further embodiments, the drainage conduits 240 may be configured in parallel, in series or of combination thereof, such as with some drainage conduits 240 being positioned in parallel and other drainage conduits 240 being positioned in series. When configured in series, the drainage conduits 240 may be interconnected by means of couplers 244 configured to allow a fluid communication between two or more drainage conduits 240. When configured in parallel, the drainage conduits 240 may be interconnected by means of a distribution device 248 configured to distribute the effluent 130 across the two or more interconnected drainage conduits 240.

In yet other embodiments, the drainage conduits 240 may comprise microbes. The microbes may allow an aerobic process to treat the effluent 130 by absorbing the organic waste, removing pathogens and breaking down the effluent 130 into soluble by-products. In an embodiment, the drainage conduits 240 are adapted to encourage the development of microbial water treating bacteria responsible for a secondary treatment of the effluent 130. In particular, the drainage conduits 240 may be adapted to maintain a controlled flow rate of the effluent 130 suitable for the growth of microbial water treating bacteria and may be geometrically configured to form spaces suitable for the growth of microbial water treating bacteria.

The drainage conduits 240 may further be corrugated to increase the structural flexibility and structural strength of said conduits 240. Understandably, the corrugation of the drainage conduits 240 may further encourage the growth of microbial cultures and may provide a greater surface area for the development of microbial water treating bacteria and increases the contact surface between the microbial water treating bacteria and the effluent 130.

Still referring to FIG. 4, the flow of the effluent 130 within the drainage conduits 240 further defines a stream direction 250 wherein the ends of the drainage conduits 240 in the direction of the stream direction 250 are defined as downstream ends 252. In some embodiments, the downstream ends 252 of the drainage conduits 240 are configured to receive one or more end caps 254 which may be detachably affixed to the drainage conduits 240 and may either partially or entirely limit the flow of the effluent 130 outside of the downstream ends 252.

In some embodiments, the leach system 220 may comprise a junction pipe 256 configured to fluidly connect the one or more drainage conduits 240 at their downstream ends 252. To that end, the junction pipe 256 may comprise any shape and length necessary to reach the downstream ends 252 of the drainage conduits 240. In some embodiments, the end caps 254 may comprise an opening configured to allow fluid access to the junction pipe 256.

The leach system 220 may further comprise one or more piezometers configured to measure and indicate the volume of the effluent 130 disposed within the drainage conduits 240. It may be appreciated that a high volume of the effluent 130 within the drainage conduits 240 may represent a malfunctioning of the wastewater treatment system 100. In such embodiment, the leach system 220 comprises a piezometer 258 connected to the junction pipe 256 with a gauge located above the surface 410. The location of the piezometer 258 generally aims at easing inspection by a user, such as a trained individual.

The leach system 220 may additionally comprise one or more vents configured to allow the circulation of air within the drainage conduits 240. The air generally improves the aerobic treatment processes performed by the microbial water treating bacteria. In such an embodiment, the leach system 220 comprises a vent 260 fluidly connected to the junction pipe 256 with an opening located above the finished ground surface 410 allowing access to the outside air or atmosphere.

In a further embodiment, the drainage conduits 240 may further comprise perforations knot shown) adapted to allow a release of the effluent 130 outside of the drainage conduits 240. In a preferred embodiment, the size of the perforations, the number of perforations and the distribution of perforations are determined based on the conditions of operation. As an example, the characteristics of the perforations may be determined to ensure a steady release of the effluent 130, to ensure leaching into the surrounding layers of the drainage field 200 and to distribute the effluent 130 along a substantial portion of the drainage conduits 240 in response to the volume of water to be disposed by the wastewater treatment system 100. It may be appreciated that a high number of perforations or perforations having large apertures may cause an undesirable amount of the effluent 130 to be released early on in the drainage conduits 240 as defined by the stream direction 250. Having too many perforation apertures or having large apertures may limit the longitudinal distribution of the effluent 130 to a first section of the drainage conduits 240. Similarly, a number of perforations being too low or perforations having small apertures may prevent a sufficient volume of the effluent 130 to be released from the conduits 240. In some embodiments, having an insufficient release of effluent 130 may cause an undesirable accumulation of the effluent 130 in the conduits 240 or flooding of the drainage conduits 240 and the wastewater treatment system 100.

In some embodiments, the leach system 220 may further comprise one or more layers of porous or filtering membranes (not shown), such as fabric membranes, adapted to wrap the drainage conduits 240 and to facilitate the leaching of the effluent 130 into the filtering medium 430. The membranes may comprise any suitable synthetic media for the leaching of fluids. The membranes may further facilitate the fixation of microbial water treating bacteria supporting treatment of the effluent 130. The membranes may further support a longitudinal distribution of the effluent 130 along the drainage conduits 240.

The effluent 130 released from the leach system 220 may be absorbed by the filtering medium 430 enveloping the leach system 220. In some embodiments, the filtering medium 430 may be adapted to neutralize pollutants disposed within the effluent 130 percolating throughout the filtering medium 430, thereby providing a third treatment of the effluent 130. These pollutants may include, but are not limited to, pathogens, nitrogen, phosphorous or any other contaminants. The filtering medium 430 may further comprise sand, organic matter (i.e. peat, sawdust) or any other suitable medium or combination known in the art capable of removing or neutralizing pollutants.

Referring back to FIG. 3, the effluent 130 treated by microbial water treating bacteria within the leach system 220 and filtered by the filtering medium 430 may be defined as treated wastewater 230.

As the treated wastewater 230 exits the filtering medium 430, the treatment of the wastewater performed by the wastewater treatment system 100 is complete. The treated wastewater may disperse into the permeable soil 440 of the drainage field 200. To that end, the wastewater treatment system 100 may be in a non-draining configuration such that the treated wastewater 230 is freely released and dissipated into the permeable soil 440 without being subsequently recollected. In some embodiments, the permeable soil 440 of the drainage field 200 comprises a porous, unsaturated soil capable of absorbing fluids. In other embodiments, the treated wastewater may disperse onto a waterproof layer (not shown) installed underneath the drainage field 200 and configured to channel the treated wastewater towards a desired wastewater outlet location. In other embodiments still, the waterproof layer may be configured to channel the treated wastewater towards a collection point thereby allowing a future collection of the treated wastewater for future uses.

Figure 5:
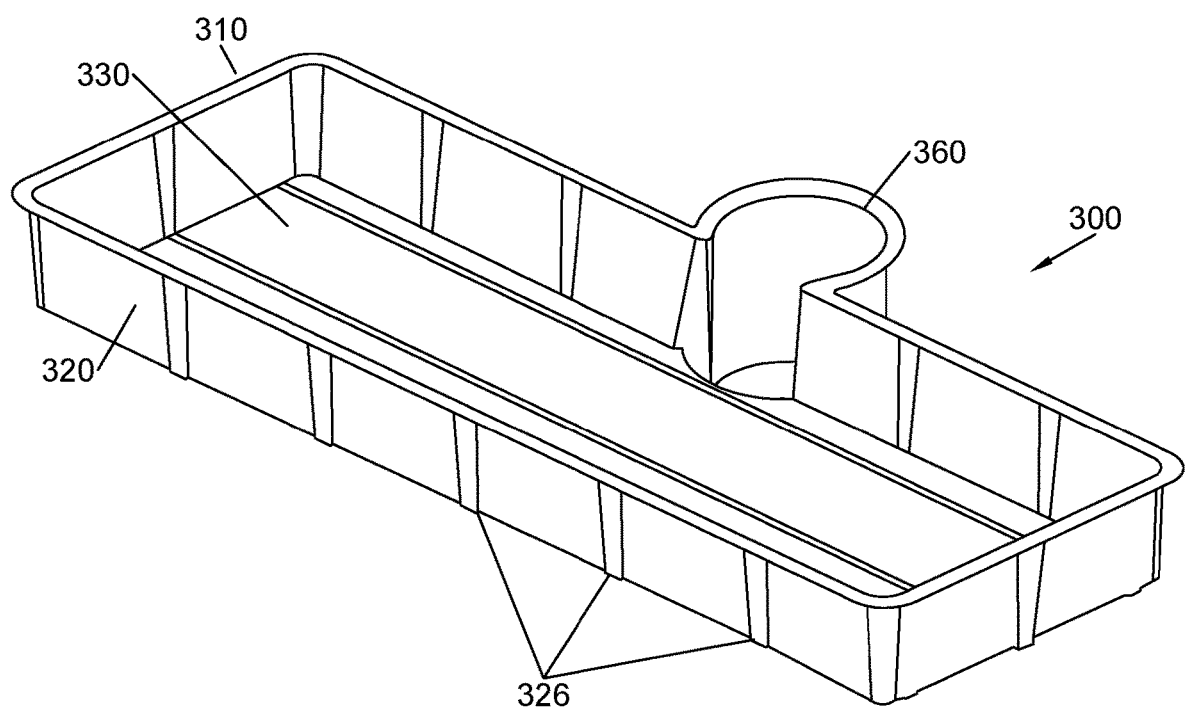
FIG. 5 is an isometric view of an exemplary sampling device used in the system of FIG. 1 shown without a sampling chimney.
Figure 6:
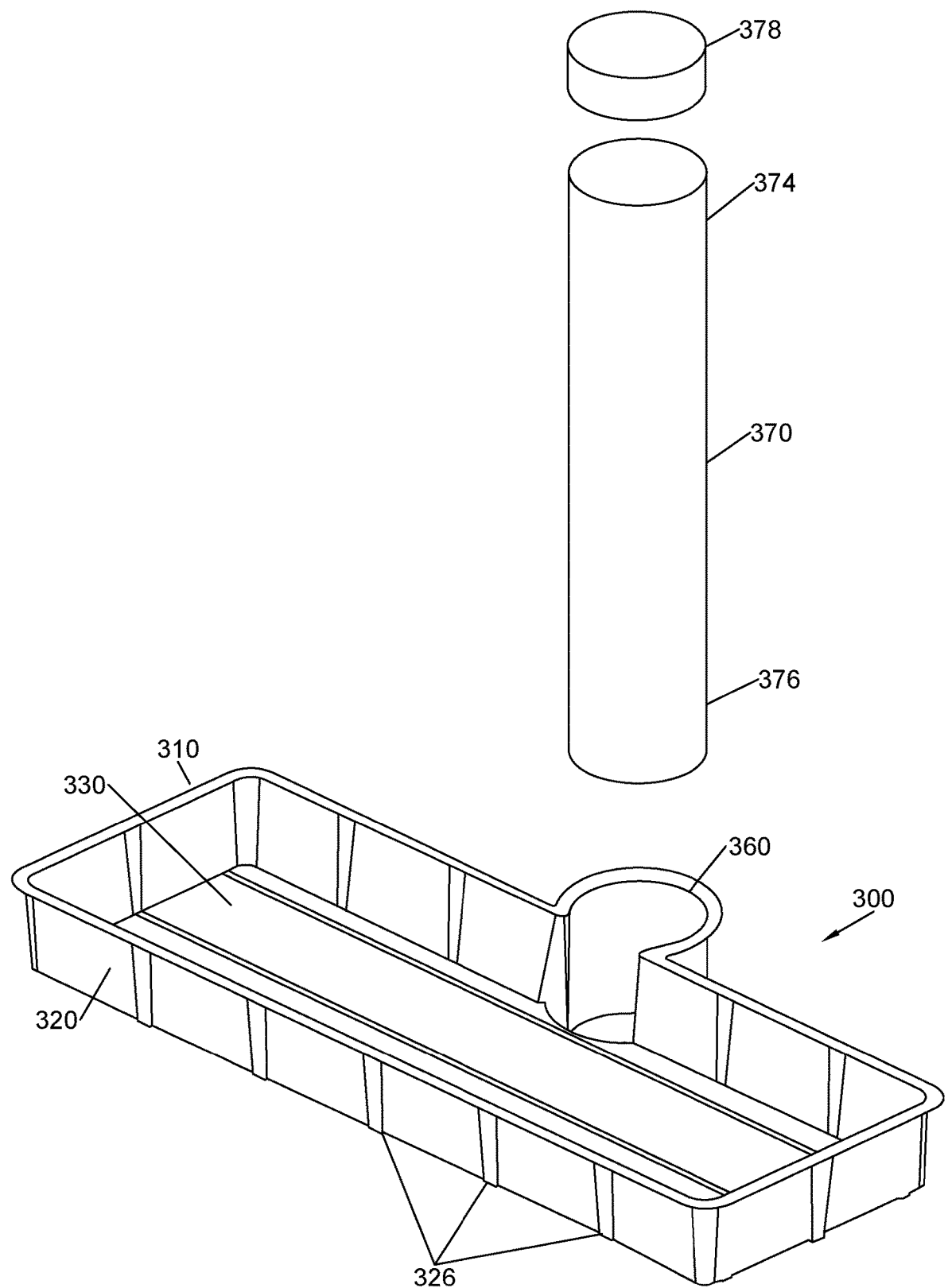
FIG. 6 is an isometric exploded view of an exemplary sampling device used in the system of FIG. 1.

Referring now to FIG. 5, an embodiment of wastewater sampling device 300 is illustrated. In some embodiments, the wastewater treatment system 100 may comprise the wastewater sampling device 300. Such device is generally configured to collect a portion of the effluent 130 and/or of the treated wastewater 230 for sampling purposes, hereinafter defined as sampling wastewater 305 (see for instance FIGS. 11, 12A and 12B). The sampling of the effluent 130 and/or of the treated wastewater 230 may be beneficial to ensure proper functioning of the wastewater treatment system 100 and compliance with possible local regulations.

The sampling device 300 may be installed in the drainage field 200. The sampling device 300 is typically buried under the leach system 220 and above the bedrock layer 450. According to the embodiment shown in FIG. 3, the sampling device 300 is disposed between the filtering medium 430 and the permeable soil layer 440. Disposed in this manner, the sampling wastewater 305 collected by the sampling device 300 may offer a clearer representation of the total treatment achieved by the wastewater treatment system 100. It may be appreciated that the sampling device 300 may be installed at any other depth within the drainage field 200 to obtain a different desired reading. As an example, in another embodiment, the sampling device 300 may be installed at a shallower depth beneath the leach system 220 to obtain sampling wastewater 305 offering a representation of the effluent 130 as it is released from the leach system 220.

In some embodiments and as shown in FIGS. 5 to 10, the sampling device 300 may comprise a base 310 and side walls 320. In this exemplary embodiment, the base 310 of the sampling device 300 has a generally rectangular shape and comprises rounded edges. Understandably, in other embodiments, the base 310 of the sampling device 300 may have a generally circular shape, oval shape, trapezoidal shape or any other shape necessary to suit the requirements of the wastewater treatment system 100 or the topographic requirements of the installation site.

The side walls 320 may be configured to rise vertically above the base 310 to form a cavity or container 330. In certain embodiments, the side walls 320 may be angled to alter the volume of the cavity 330. In a preferred embodiment and as shown in FIGS. 5 to 10, the side walls 320 may be connected at the intersection of two or more side walls 320 to form a continuous wall. The connection of two or more side walls 320 generally tends to increase the structural rigidity of the sampling device 300. The base 310 and side walls 320 may further comprise one or more ribs 326 adapted to increase the structural rigidity of the side walls 320.

In some embodiments, the base 310 and side walls 320 may be made of any rigid and impermeable material. The impermeable materials may include, but are not limited to, fiberglass, plastics such as polypropylene and polyethylene, fibrous material, metal, rubber, rubber-like materials or any other suitable material known in the art. Understandably, the base 310 and side walls 320 may be made of different portions or may be unitary.

It may be appreciated that the structural integrity of the base 310 and side walls 320 generally allow installing the sampling device 300 on many types of surfaces without requiring additional support structures or components. As such, the sampling device 300 may be installed in a wide range of possible locations and depths.

In some embodiments and as shown in FIGS. 5 to 12, the side walls 320 may further comprise one or more flanges 322. The flange may be extending substantially horizontally and outwardly with respect to the cavity 330. The flanges 322 may be configured to provide additional support and stability to the sampling device 300 following its installation by providing additional support surfaces to the sampling device 300.

In embodiments of sampling device 300 being installed in the drainage field 200, the cavity 330 may be partially or entirely filled with soil or material from the covering layer 420, the filtering medium 430, the permeable soil layer 440 or any combination thereof. The soil or material disposed within the cavity may be defined as the sampling material (not shown).

Figure 7:
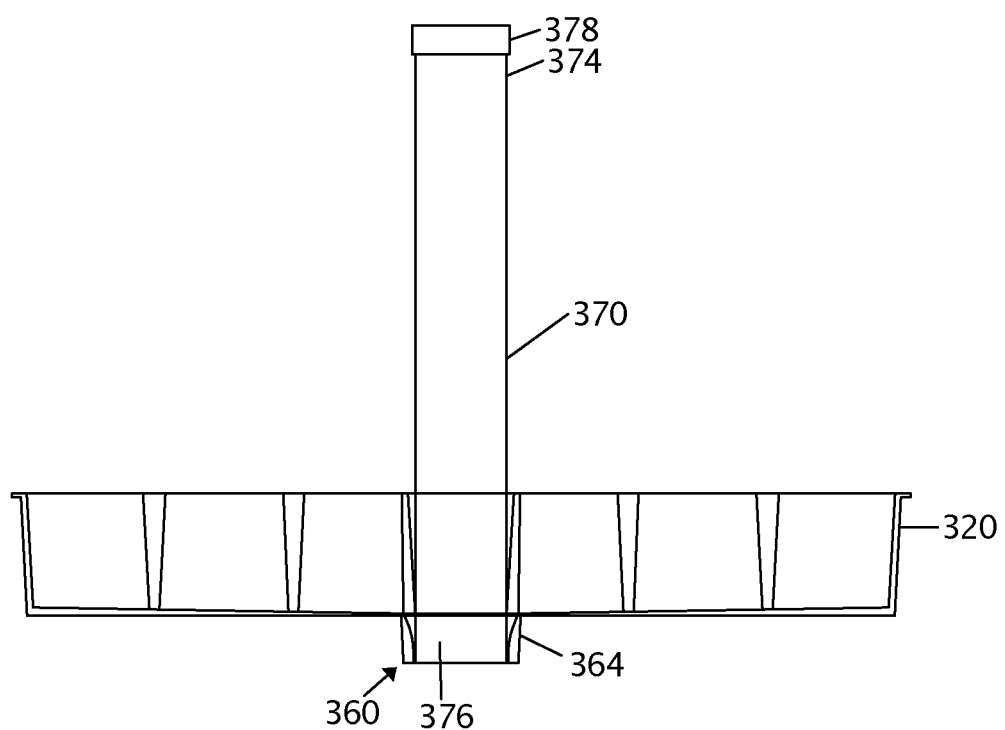
FIG. 7 is a front perspective view of the sampling device of FIG. 6.
Figure 8:
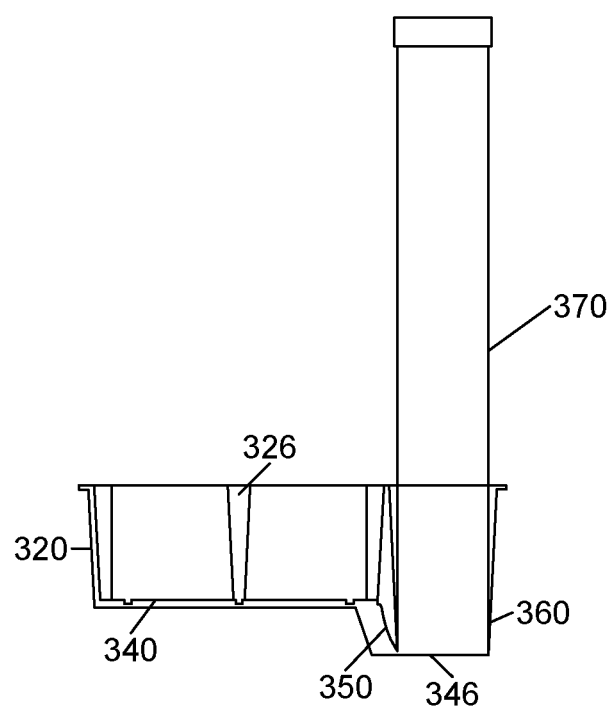
FIG. 8 is a side perspective view of the sampling device of FIG. 6.
Figure 9:
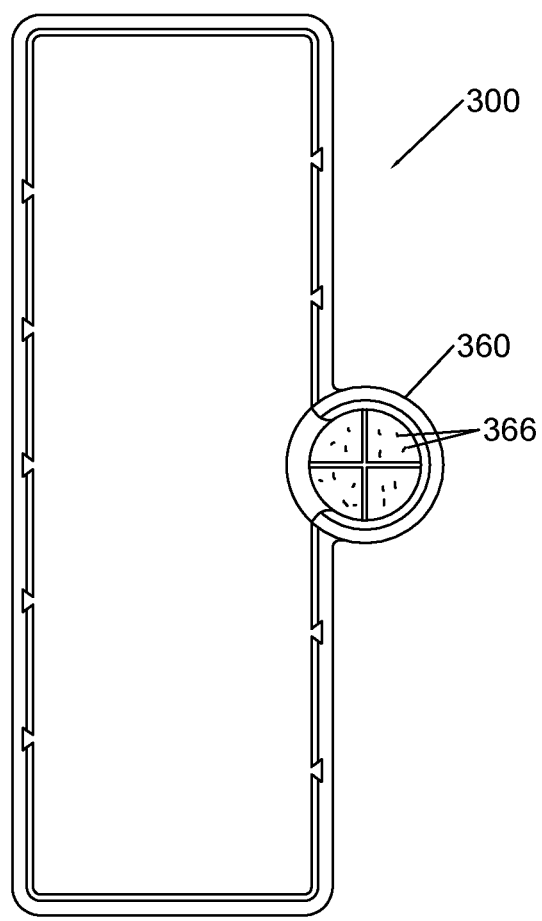
FIG. 9 is a top perspective view of the sampling device of FIG. 6.
Figure 10:
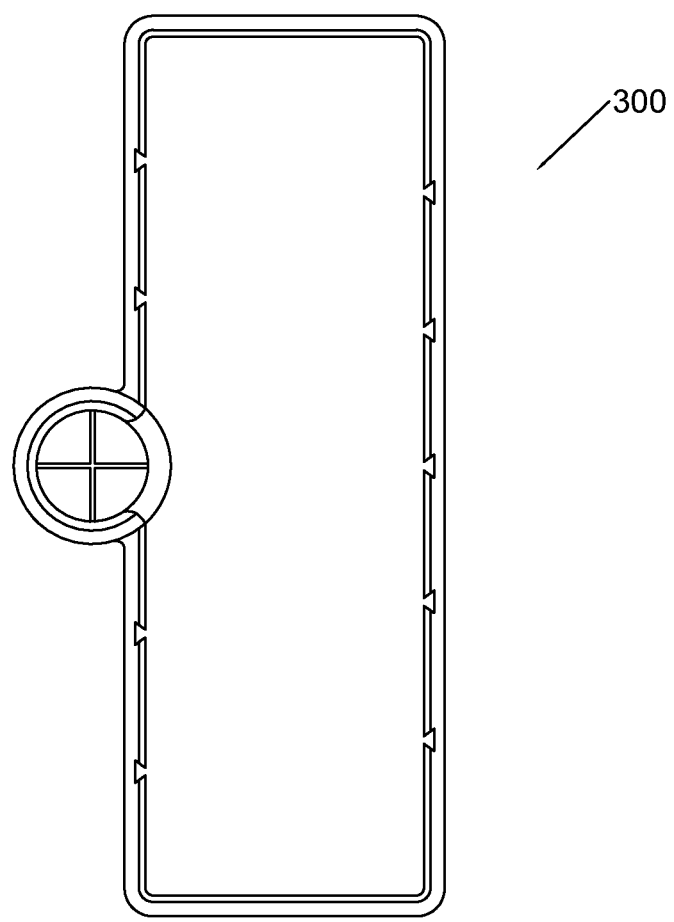
FIG. 10 is a bottom perspective view of the sampling device of FIG. 6.

Referring now to FIGS. 5 to 10, an embodiment of the base 310 may comprise an upper portion 340 and one or more lower portions 346 wherein the upper portion 340 is disposed on a plane located above the one or more lower portions 346. The base 310 may additionally comprise a ramp 350 creating an angled surface separating the upper portion 340 and the one or more lower portions 346. The angled surface of the ramp 350 may comprise any angle suitable for conveying fluid from the upper portion 340 to the one or more lower portions 346. In some embodiments, the upper portion 340, the one or more lower portions 346 and the ramp 350 may comprise distinct and/or different surfaces. Referring now to FIGS. 7 and 8, the embodiment of the sampling device 300 comprises an upper portion 340, a lower portion 346 and a ramp 350. In certain embodiments, the width of the ramp 350 may comprise a width being similar to that of the lower portion 346.

Referring back to FIGS. 5 to 10, the one or more lower portions 346 may further comprise one or more collection wells 360 configured to collect the sampling wastewater 305 percolating through the sampling material and flowing through the sampling device 300. In some embodiments, the sampling device 300 comprises a collection well 360 and a collection well base 364 defined by the bottom surface of the collection well 360. In such embodiment, the upper portion 340 and the ramp 350 are disposed to direct the sampling wastewater 305 percolating through the sampling material. As such, the sampling wastewater 305 is conveyed into the collection well 360 by gravitational forces and the geometry of the sampling device 300. In some embodiments, the upper portion 340 may be angled to direct the sampling wastewater 305 towards the collection well 360. The wastewater 305 may be conveyed at the periphery of the chimney 370 inserted in the well 360.

Figure 12A:
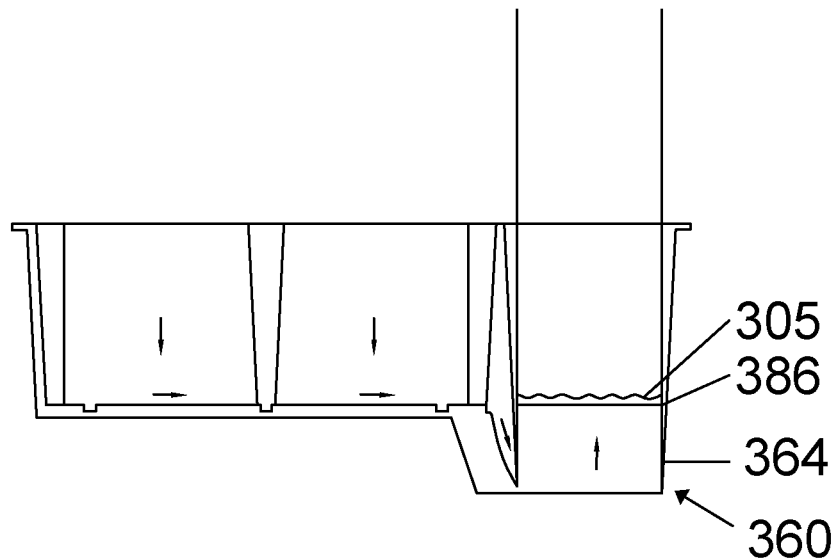
FIG. 12A is a side perspective view of the sampling device of FIG. 6 illustrating the directional flow of the sampling wastewater into the sampling chimney.
Figure 12B:
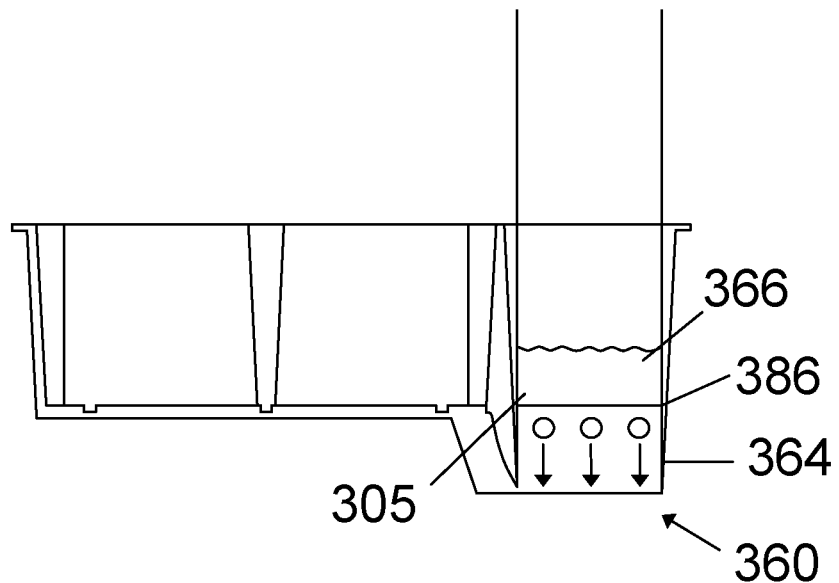
FIG. 12B is a side perspective view of the sampling device of FIG. 6 illustrating the directional flow of the sampling wastewater out of the collection well.
Figure 13:
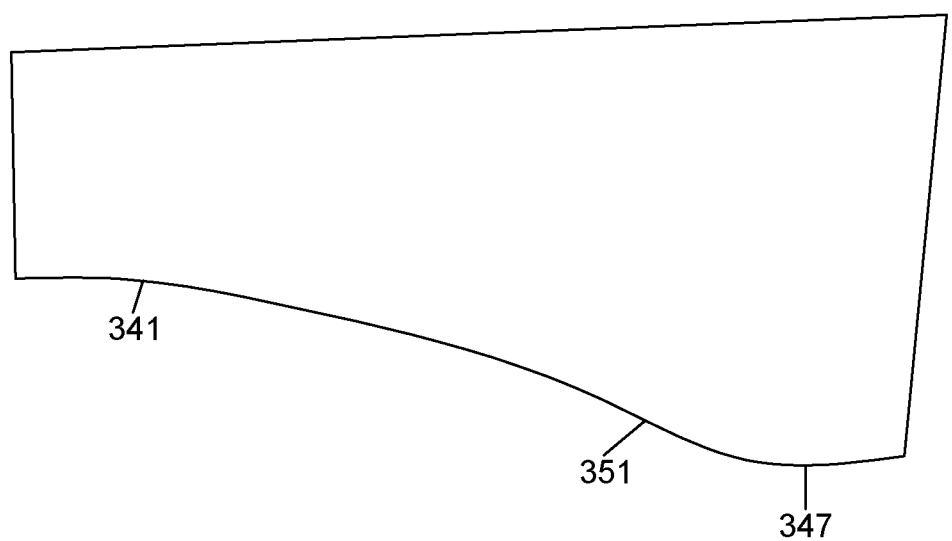
FIG. 13 is a side view of another embodiment of a sampling device.

Referring now to FIGS. 7, 12A and 12B, the collection well base 364 may further comprise base perforations or apertures 366. The perforations 366 are generally configured to allow a release of the sampling wastewater 305 into the soil around or beneath the sampling device 300. In the present embodiment, the base perforations 366 are configured to allow a steady release and leaching of the sampling wastewater 305 into the surrounding layers of the drainage field 200.

Figure 11:
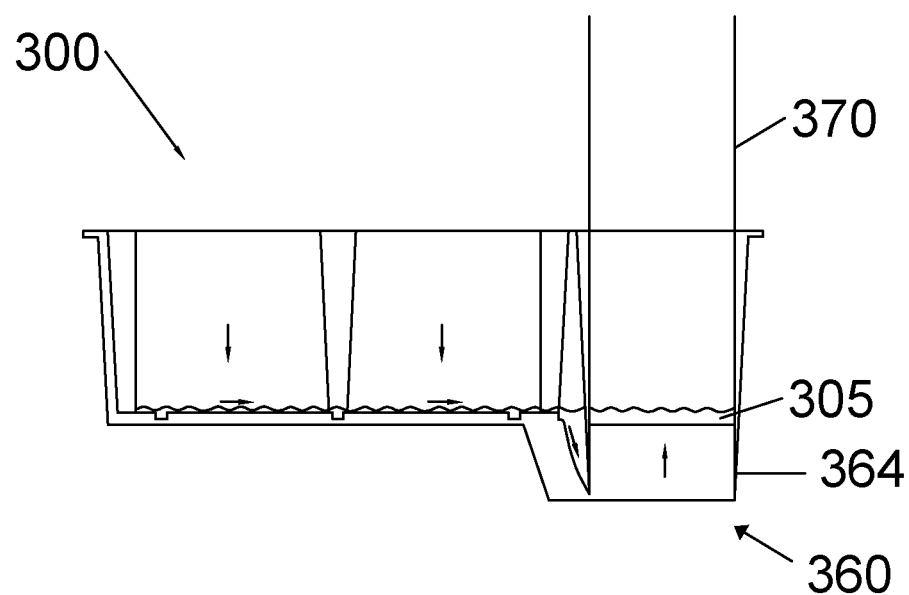
FIG. 11 is a side perspective view of the sampling device of FIG. 6 illustrating the directional flow of the sampling wastewater within the sampling device.

Referring now to FIGS. 7 and 11, the collection well base 364 may further comprise base perforations or apertures 366. The perforations 366 are generally configured to allow a release of the sampling wastewater 305 into the soil beneath the sampling device 300. In the present embodiment, the base perforations 366 are configured to allow a steady release and leaching of the sampling wastewater 305 into the surrounding layers of the drainage field 200.

Referring now to FIGS. 6 to 8 and 11 to 12B, the sampling device 300 may further comprise one or more collection chimneys 370 configured to facilitate access to the sampling wastewater 305 disposed within the one or more collection wells 360. The one or more collection chimneys 370 may have a longitudinal cross-section shaped as a circle, oval, rectangular, shape or any other suitable shape. The collection chimney may be made of any semi-rigid material or hard but pliable material, such as but not limited to plastics, such as polypropylene and polyethylene, other types of polymers, fibrous material, metal, rubber or rubber-like materials or any combination thereof. The one or more collection chimneys 370 may further be corrugated to increase their structural flexibility and structural strength.

Referring now to FIGS. 5 to 10, an embodiment of the sampling device 300 having a collection chimney 370 is shown. The collection chimney 370 is in fluid communication with the collection well 360. The one or more sampling chimney 370 may have any length suitable for allowing access to the sampling wastewater 305 present in the collection well 360. The collection chimney 370 may advantageously allow access to the sampling wastewater 305 from above the surface 410 or with little or no digging below the surface 410.

The collection chimney 370 may further be have a diameter suitable for allowing access to the sampling wastewater 305 located within the collection well 360 with a liquid collection device (not shown). Examples of liquid collection devices include, but are not limited to, pipettes, vacuum tubes, ladles, or any other means of collecting fluids.

Referring now to FIG. 3, an embodiment of the collection chimney 370 that extends substantially from the base 310 is shown. The collection chimney 370 may comprise an upper end 374 and a lower end 376. The upper end 374 may comprise a chimney cap 378 configured to prevent any substance, such as rain water, debris or any other contaminant, from entering the collection chimney 370. Such substance may, in some circumstances, contaminate the sampling wastewater 305 located within the collection well 360. The chimney cap 378 may entirely or partially seal the upper end 374 of the chimney cap 378.

In another embodiment, the upper end 374 of the sampling chimney 370 may be located below the surface 410 and may be accessible by other means such as digging beneath the finished ground surface 410, a hatch system, a recess in the ground or any other known means.

In some further embodiments, the collection well 360 may be shaped or may comprise resilient members (not shown) to force or squeeze against the periphery of the chimney 370, thus maintaining the base or lower end 376 of the chimney 370 into place. Understandably, any other mean to maintain the lower end 376 of the chimney 370 into the collection wells 360 may be used within the scope of the present invention.

Referring now to FIGS. 12A and 12B, an embodiment of the sampling device 300 comprising a filter 386 is shown. The filter is generally adapted to separate the sampling material or any other solid matter located within the cavity 330 of the sampling device 300 from a portion or the entirety of the sampling wastewater 305 disposed within the collection well 360. The filter 386 comprises a porous medium or any other porous device configured to filter impurities or solid particles from the sampling, such as a metallic mesh screen or a woven fabric. In the illustrated embodiment, the lower end 376 of the sampling chimney 370 comprises a filter 386 which covers the opening created by the sampling chimney 370.

It may be appreciated that the sampling device 300 may receive an increased volume of sampling wastewater 305 as the wastewater flow rate delivered by the drainage pipe 110 increases. In such situations and as shown in FIG. 12A, the sampling wastewater 305 percolates through the sampling material 334 located within the sampling device 300 and is subsequently guided by gravitational forces and the geometry of the sampling device 300, into the collection well 360. Pressure equilibrium and capillary forces may subsequently force the sampling wastewater 305 upwards through the filter 386 and into the sampling chimney 370. Referring now to FIG. 12B, in some embodiments, as the level of the sampling wastewater 305 raises above the perforations 366, the sampling wastewater 305 may be conveyed outside of the collection well 360 and released into surrounding layers of the drainage field 200. In another embodiment and as illustrated in FIG. 7, the perforations 366 may be disposed on the collection well base 364 such that, when the wastewater flow rate delivered by the drainage pipe 110 decreases, the sampling wastewater 305 disposed within the sampling chimney 370 may be guided by gravitational forces downwards through the base perforations 366 in the collection well base 364 and be released into surrounding layers of the drainage field 200.

It may further be appreciated that capillary forces generated by the porosity of the covering layer 420, the filtering medium 430, the permeable soil layer 440 and/or the sampling material may convey a portion or the entirety of the sampling wastewater 305 outside of the cavity 330. This dispersion of the sampling wastewater 330 may be undesirable as it may limit the volume of the sampling wastewater 305 captured by the sampling device 300 for sampling. To that end, the side walls 320 may be configured to extend vertically above the base 310 such as to prevent, in conjunction with gravitational forces, the sampling wastewater 305 from being conveyed outside of the cavity 330. In a preferred embodiment, the side walls 320 may extend vertically above the base 310 a height of at least 25 cm to limit the dispersion of the sampling wastewater 305 outside of the cavity 330 and to retain a suitable volume of the sampling wastewater 305 for collection within the sampling chimney 370.

While illustrative and presently preferred embodiments of the invention have been described in detail hereinabove, it is to be understood that the inventive concepts may be otherwise variously embodied and employed and that the appended claims are intended to be construed to include such variations except insofar as limited by the prior art.

The invention claimed is:

1. A wastewater treatment sampling device configured for installation underneath of a non-draining wastewater treatment system and for the collection of a sample of wastewater originating from the wastewater treatment system, the wastewater treatment sampling device comprising:
   a container configured to capture the sampling wastewater under a wastewater treatment system, the container comprising:
      a base comprising a surface area being smaller than a surface area of a leach system of the wastewater treatment system; and
      side walls vertically extending from the base by a height suitable to prevent the received sampling wastewater from being conveyed outside of the container;
   a collection well downwardly extending from the base, the collection well being adapted to collect the captured sampling wastewater channelled from the container; and
   a sampling chimney in fluid communication with the collection well and adapted to allow access to the sampling wastewater collected within the collection well.

2. The wastewater treatment sampling device of claim 1, wherein the container and the collection well are unitary.

3. The wastewater treatment sampling device of claim 1, wherein the side walls comprise flanges.

4. The wastewater treatment sampling device of claim 1, the sampling chimney comprising a lower base portion in fluid communication with the collection well.

5. The wastewater treatment sampling device of claim 4, the lower base portion comprising a filter.

6. The wastewater treatment sampling device of claim 5, the lower base portion comprising an opening, the filter stretching over the opening.

7. The wastewater treatment sampling device of claim 1, wherein the base comprises ribs.

8. The wastewater treatment sampling device of claim 1, wherein the side walls comprise ribs.

9. The wastewater treatment sampling device of claim 1, wherein the wastewater treatment sampling device comprises a ramp adapted to channel sampling wastewater from the container to the collection well.

10. The wastewater treatment sampling device of claim 1, wherein the collection well comprises a perforated surface adapted to allow a release of the sampling wastewater from the collection well.

11. The wastewater treatment sampling device of claim 10, wherein the collection well base is lower than the base of the container.

12. The wastewater treatment sampling device of claim 10, wherein the perforated surface comprises perforations located beneath the base.

13. The wastewater treatment sampling device of claim 1, the container being made of semi-rigid material.

14. The wastewater treatment sampling device of claim 13, the sampling device being made of plastic.

15. The wastewater treatment sampling device of claim 1, the side walls forming a continuous wall.

16. The wastewater treatment sampling device of claim 1, the collection well extending from a side wall.

17. The wastewater treatment sampling device of claim 1, the side walls vertically extending above the base by a height of at least 25 cm.

18. A method of collecting treated wastewater for sampling from a leach system of a non-draining wastewater treatment system comprising:
   capturing in a container of a sampling device some of the treated wastewater originating from a portion of the leach system of the wastewater treatment system;
   channelling the captured wastewater from the container of the sampling device to a collection well using a ramp at an angle; and
   collecting the channelled wastewater through a collection chimney in fluid communication with the collection well for testing the treatment system.

19. The method as claimed in claim 18, the method further comprising filtering the channelled wastewater.

20. The method as claimed in claim 18, channelling the collected wastewater from the container of the sampling device around the chimney inserted into the collection well.

21. The method as claimed in claim 18, channelling the collected wastewater from the container of the sampling device below the chimney inserted into the collection well.

22. The method as claimed in claim 18, the method further comprising burying the sampling device under a drainage field.

23. The method as claimed in claim 18, the method further comprising testing the wastewater treatment system.

24. A wastewater treatment sampling device configured for installation underneath a portion of a non-draining wastewater treatment system and for the collection of a sample of wastewater present in the wastewater treatment system, the wastewater treatment sampling device comprising:
   a container made of semi-rigid material to capture the sampling of wastewater under the wastewater treatment system, the container comprising:
      a base comprising a surface area being smaller than a surface area of a leach system of the wastewater treatment system;
      side walls comprising flanges, the side walls vertically extending from the base by a height suitable to prevent the received sampling wastewater from being conveyed outside of the container;
      a collection well downwardly extending from the base, the collection well being adapted to collect the captured sampling wastewater channelled from the container;
      a ramp adapted to channel sampling wastewater from the base to the collection well; and
   a sampling chimney comprising a lower base portion in fluid communication with the collection well and adapted to allow access to the sampling wastewater collected within the collection well.

25. The wastewater treatment sampling device of claim 24, wherein the collection well comprises a perforated surface adapted to allow a release of the sampling wastewater from the collection well.

* * * * *